United States Patent
Coleman et al.

(10) Patent No.: US 11,302,431 B2
(45) Date of Patent: *Apr. 12, 2022

(54) SYSTEMS AND METHODS FOR QUANTIFICATION AND PRESENTATION OF MEDICAL RISK ARISING FROM UNKNOWN FACTORS

(71) Applicant: Invitae Corporation, San Francisco, CA (US)

(72) Inventors: Howard C. Coleman, Seattle, WA (US); Robert D. Patterson, Lexington, MA (US); Jessica Oesterheld, Bath, ME (US); Rajeev V. Pany, Issaquah, WA (US); Kristine Ashcraft, Burien, WA (US)

(73) Assignee: Invitae Corporation, San Francisco, CA (US)

( * ) Notice: Subject to any disclaimer, the term of this patent is extended or adjusted under 35 U.S.C. 154(b) by 321 days.

This patent is subject to a terminal disclaimer.

(21) Appl. No.: 16/264,397

(22) Filed: Jan. 31, 2019

(65) Prior Publication Data

US 2019/0164637 A1    May 30, 2019

Related U.S. Application Data

(63) Continuation of application No. 14/170,367, filed on Jan. 31, 2014, now Pat. No. 10,210,312.

(Continued)

(51) Int. Cl.
*G16H 20/13* (2018.01)
*G16H 50/30* (2018.01)
(Continued)

(52) U.S. Cl.
CPC ............. *G16H 20/13* (2018.01); *G16C 20/30* (2019.02); *G16H 20/10* (2018.01); *G16H 50/30* (2018.01); *G16H 70/40* (2018.01)

(58) Field of Classification Search
CPC ........ G16H 20/13; G16H 50/30; G16H 70/40; G16H 20/10
(Continued)

(56) References Cited

U.S. PATENT DOCUMENTS 5,758,095 A    5/1998  Albaum
5,833,599 A *  11/1998 Schrier ................. G16H 70/40
                                                   600/300
(Continued)

FOREIGN PATENT DOCUMENTS

WO    2002086663 A2    10/2002
WO    2003008637 A2    1/2003
(Continued)

OTHER PUBLICATIONS

Obach et al. (The Utility of in Vitro Cytochrome P450 Inhibition Data in the Prediction of Drug-Drug Interactions, 2006, The American Society for Pharmacology and Experimental Therapeutics, pp. 336-348) (Year: 2006).*

(Continued)

*Primary Examiner* — Iftekhar A Khan
(74) *Attorney, Agent, or Firm* — Sterne, Kessler, Goldstein & Fox P.L.L.C.

(57) ABSTRACT

Example methods of quantifying known and unknown risks of an adverse drug event in an individual based on various factors are disclosed. In some embodiments, factors include known drug-drug interactions and unknown phenotypes of cytochromes. Quantification may be based on severity of the adverse drug event/and or probability of occurrence in some embodiments. Example methods of displaying the quantified risk are also disclosed. In one embodiment, the risk of individuals is aggregated to display the risk of a population.

20 Claims, 13 Drawing Sheets

Related U.S. Application Data

(60) Provisional application No. 61/771,850, filed on Mar. 2, 2013, provisional application No. 61/760,162, filed on Feb. 3, 2013.

(51) Int. Cl.
  *G16C 20/30* (2019.01)
  *G16H 70/40* (2018.01)
  *G16H 20/10* (2018.01)

(58) Field of Classification Search
  USPC .................................................. 703/2
  See application file for complete search history.

(56) References Cited

U.S. PATENT DOCUMENTS

| | | | |
|---|---|---|---|
| 5,842,173 A | 11/1998 | Strum | |
| 5,845,255 A | 12/1998 | Mayaud | |
| 5,960,411 A | 9/1999 | Hartman | |
| 6,063,026 A | 5/2000 | Schauss et al. | |
| 6,317,719 B1 | 11/2001 | Schrier | |
| 6,528,260 B1* | 3/2003 | Blumenfeld | C12Q 1/6827 435/4 |
| 6,789,091 B2 | 9/2004 | Gogolak | |
| 6,968,513 B1 | 11/2005 | Reinbold et al. | |
| 7,054,755 B2 | 5/2006 | O'Reilly | |
| 7,054,758 B2 | 5/2006 | Gill-Garrison | |
| 7,058,616 B1 | 6/2006 | Larder | |
| 7,089,498 B1 | 8/2006 | Rathjen | |
| 7,235,358 B2* | 6/2007 | Wohlgemuth | C12Q 1/6881 435/6.1 |
| 7,266,839 B2 | 9/2007 | Bowers et al. | |
| 7,542,961 B2 | 6/2009 | Gogolak | |
| 7,747,392 B2* | 6/2010 | Ruano | G16B 20/20 702/19 |
| 7,844,469 B2 | 11/2010 | Holden | |
| 7,925,612 B2 | 4/2011 | Gogolak | |
| 8,099,298 B2 | 1/2012 | Coleman | |
| 8,311,851 B2 | 11/2012 | Patterson | |
| 8,401,801 B2 | 3/2013 | Mrazek et al. | |
| 8,589,175 B2* | 11/2013 | Glauser | G16B 40/00 705/2 |
| 8,676,608 B2* | 3/2014 | Oesterheld | G16C 20/50 705/3 |
| 10,210,312 B2* | 2/2019 | Coleman | G16H 70/40 |
| 10,240,205 B2* | 3/2019 | Hatchwell | G01N 33/56983 |
| 10,961,585 B2* | 3/2021 | Hatchwell | C12Q 1/6883 |
| 2002/0002473 A1 | 1/2002 | Schrier | |
| 2002/0010595 A1 | 1/2002 | Kapp | |
| 2002/0012921 A1* | 1/2002 | Stanton, Jr. | G16H 20/70 435/6.16 |
| 2002/0039990 A1* | 4/2002 | Stanton, Jr. | C12Q 1/6883 514/1 |
| 2002/0049772 A1 | 4/2002 | Rienhoff | |
| 2002/0076664 A1 | 6/2002 | Yan | |
| 2002/0076774 A1* | 6/2002 | Yan | C12N 9/00 435/183 |
| 2002/0082869 A1* | 6/2002 | Anderson | G06Q 10/10 705/3 |
| 2002/0095313 A1 | 7/2002 | Haq | |
| 2002/0173993 A1 | 11/2002 | Skulason | |
| 2003/0023385 A1* | 1/2003 | Lazaridis | G16B 40/00 702/19 |
| 2003/0023387 A1 | 1/2003 | Gill-Garrison | |
| 2003/0046110 A1* | 3/2003 | Gogolak | G16B 20/40 705/2 |
| 2003/0054394 A1 | 3/2003 | Chin et al. | |
| 2003/0104453 A1 | 6/2003 | Pickar et al. | |
| 2003/0135096 A1 | 7/2003 | Dodds | |
| 2003/0211486 A1* | 11/2003 | Frudakis | C12Q 1/6883 435/6.16 |
| 2003/0219149 A1 | 11/2003 | Vailaya et al. | |
| 2003/0233218 A1* | 12/2003 | Schilling | G16B 5/00 703/11 |
| 2004/0082000 A1* | 4/2004 | Stanton, Jr. | G16H 10/40 435/6.16 |
| 2004/0084867 A1 | 5/2004 | Leyland-Jones | |
| 2004/0088191 A1 | 5/2004 | Holden | |
| 2004/0098286 A1 | 5/2004 | Zimmerman | |
| 2004/0132771 A1 | 7/2004 | Babcock et al. | |
| 2004/0171056 A1* | 9/2004 | Stanton, Jr. | C12Q 1/6883 435/6.16 |
| 2004/0193446 A1* | 9/2004 | Mayer | G16H 20/10 705/2 |
| 2004/0197813 A1 | 10/2004 | Hoffman | |
| 2004/0199333 A1 | 10/2004 | Hoffman | |
| 2004/0241714 A1 | 12/2004 | Branch et al. | |
| 2005/0049656 A1 | 3/2005 | Peterson et al. | |
| 2005/0060102 A1* | 3/2005 | O'Reilly | G16B 50/00 702/20 |
| 2005/0086035 A1* | 4/2005 | Peccoud | G16B 20/20 703/2 |
| 2005/0149361 A1 | 7/2005 | Saus | |
| 2005/0154627 A1 | 7/2005 | Zuzek et al. | |
| 2005/0191691 A1* | 9/2005 | Stanton, Jr. | C12Q 1/6886 435/6.16 |
| 2006/0063156 A1* | 3/2006 | Willman | A61P 35/02 435/6.14 |
| 2006/0160074 A1* | 7/2006 | Dorn | C12Q 1/6888 435/6.11 |
| 2006/0178837 A1 | 8/2006 | Gill-Garrison | |
| 2006/0278241 A1* | 12/2006 | Ruano | G16H 10/20 128/898 |
| 2006/0280786 A1* | 12/2006 | Rabinow | A61K 9/0019 424/450 |
| 2006/0289019 A1* | 12/2006 | Marchand | G16H 20/10 128/898 |
| 2007/0003931 A1 | 1/2007 | Mrazek et al. | |
| 2007/0004039 A1 | 1/2007 | Liu et al. | |
| 2007/0016390 A1* | 1/2007 | Bernardo | G16B 20/20 703/11 |
| 2007/0135997 A1* | 6/2007 | Hytopoulos | G01N 33/5041 702/19 |
| 2007/0166707 A1* | 7/2007 | Schadt | C12Q 1/6883 435/6.11 |
| 2007/0185124 A1 | 8/2007 | Hofland et al. | |
| 2007/0250462 A1* | 10/2007 | Wilson | G01N 33/6893 706/13 |
| 2008/0075722 A1* | 3/2008 | DePinho | C12Q 1/6837 424/138.1 |
| 2008/0215402 A1 | 9/2008 | Pearson et al. | |
| 2008/0311563 A1* | 12/2008 | Mrazek | A61P 25/24 435/6.12 |
| 2009/0094059 A1* | 4/2009 | Coleman | G16H 20/10 705/3 |
| 2009/0138286 A1 | 5/2009 | Linder | |
| 2009/0215812 A1 | 5/2009 | Bedrosian et al. | |
| 2009/0171697 A1* | 7/2009 | Glauser | G16H 70/40 705/3 |
| 2009/0299645 A1* | 12/2009 | Colby | G16H 50/30 702/19 |
| 2009/0307181 A1* | 12/2009 | Colby | G16B 20/20 706/54 |
| 2010/0022406 A1* | 1/2010 | Srinivasan | G16B 20/40 506/9 |
| 2010/0099087 A1* | 4/2010 | Stanton, Jr. | C12Q 1/6883 435/6.11 |
| 2011/0082867 A1* | 4/2011 | Bruns | G16B 20/00 707/748 |
| 2011/0119212 A1* | 5/2011 | De Bruin | G16H 50/70 706/12 |
| 2012/0015357 A1* | 1/2012 | Suhre | C12Q 1/6883 435/6.11 |
| 2012/0016594 A1* | 1/2012 | Christman | G16B 50/00 702/19 |
| 2012/0078657 A1* | 3/2012 | Patterson | G16C 20/50 705/2 |
| 2012/0116799 A1* | 5/2012 | Lindskog | G16H 70/20 705/2 |

(56) References Cited

U.S. PATENT DOCUMENTS

| | | | |
|---|---|---|---|
| 2013/0041683 A1* | 2/2013 | Boissel | G16B 5/20 |
| | | | 705/2 |
| 2013/0090909 A1* | 4/2013 | Dudley | G16H 50/00 |
| | | | 703/11 |
| 2014/0142986 A1 | 5/2014 | Oesterheld et al. | |
| 2014/0222400 A1* | 8/2014 | Coleman | G16C 20/30 |
| | | | 703/2 |
| 2014/0349320 A1* | 11/2014 | Bisson | G01N 33/5695 |
| | | | 435/7.92 |
| 2015/0240315 A1* | 8/2015 | Blakemore | G16B 5/00 |
| | | | 514/265.1 |
| 2016/0004838 A1* | 1/2016 | Patterson | G06F 17/10 |
| | | | 703/2 |
| 2020/0402614 A1* | 12/2020 | Spencer | G06N 3/002 |

FOREIGN PATENT DOCUMENTS

| | | |
|---|---|---|
| WO | 2003008637 A3 | 1/2003 |
| WO | 2003021389 A2 | 3/2003 |
| WO | 2004033722 A2 | 4/2004 |
| WO | 2005038049 A2 | 4/2005 |
| WO | 2005038049 A3 | 4/2005 |
| WO | 2007064675 A2 | 6/2007 |
| WO | 2008017038 A2 | 2/2008 |
| WO | 2009108802 A2 | 9/2009 |
| WO | 2014121133 | 8/2014 |
| WO | 2016003514 A1 | 1/2016 |

OTHER PUBLICATIONS

Elizabeth McPherson (Genetic Diagnosis and Testing in Clinical Practice, 2006, Clinical Medicine & Research, pp. 123-129) (Year: 2006).*

Galetin et al. (Prediction of Time-Dependent CYP3A4 Drug-Drug Interactions: Impact of Enzyme Degradation, Parallel Elimination Pathways, and Intestinal Inhibition, 2006, The American Society for Pharmacology and Experimental Therapeutics, pp. 166-175) (Year: 2006).*

Evans et al. (Pharmacogenomics: The Inherited Basis for Interindividual Differences in Drug Response, 2001, Annual Reviews, pp. 9-39) (Year: 2001).*

First Office Action dated Jun. 14, 2018 for EP Appl. No. 14708143.4.

Lack of unity rejection issued Jul. 9, 2014 for PCT appln No. PCT/US2014/014285.

International Search Report and Written Opinion for PCT/US2014/014285 dated Sep. 18, 2014.

Bond, CA et al., "Adverse drug reactions in United States hospitals", Pharmacotherapy, 2006, 26:601-08.

Brockmoller, J. et al., "Pharmacogenitic diagnostics of cytochrome P450 polymorphisms in clinical drug development and in drug treatment", Pharmagenomics, 2000, 1:125-51.

Evans, WE et al., "Pharmacogenitics: translating functional genomics into rational therapeutics", Science, 286:487-91, 1999, 286:487-91.

Evans and Johnson, "Pharmacogenomics: the inherited basis for interindividual differences in drug response", Ann Rev Genomics and Human Genetics, 2001, 2:9-39.

Galetin, Aleksandra et al., "Prediction of Time-Dependant CYP3A4 Drug-Drug Interactions: Impact of Enzyme Degradation, Parallel Elimination Pathways, and Intestinal Inhibition", Drug Metabolism and Disposition, Copyright © 2006 by The American Society for Pharmacology and Experimental Therapeutics, vol. 34, No. 1, 2006, 166-175.

Gurwitz, D. et al., "Primum non nocere: adverse drug events must be taken seriously", Pharmacogenomics, 2007, 8:311-314.

Ichikawa, Y., "Single nucleotide polymorphism to disclose severe side-effects or proper dosage for each patient", Internal Med., 2000, 39:523-24.

Kirchheiner, J et al., "Contributions of CYP2D6, CYP2C9 and CYP2C19 to the biotransformation of E- and Z-doxepin in healthy volunteers", Pharmacogenetics, 2002, 12:571-580.

Kirchheiner, J et al., "CYP2D6 and CYP2C19 genotype-based dose recommendations for antidepressants", Acta Psychiatrica Scandinavica, 2001, 104:173-92.

Kirchheiner, J et al., "Pharmacogenetics-based therapy recommendations—ready for clinical practice", Nature Rev, 2005, 4(8):639-47.

Mcwilliam, A et al., "Health care savings from personalizing medicine using genetic testing: the case of Warfarin", AEI-Brookings Joint Center for Regulatory Studies, Working Paper, Nov. 2006, 6-23.

Obach, Scott et al., "The Utility of in Vitro Cytochrome P450 Inhibition Data in the Prediction of Drug-Drug Interactions", The Journal of Pharmacology and Experimental Therapeutics, Copyright © 2006 by The American Society for Pharmacology and Experimental Therapeutics, vol. 316, No. 1, 2006, 336-348.

Phillips, KA et al., "Potential role of pharmacogenomics in reducing adverse drug reactions: a systematic review", JAMA 286 (18):, 2001, 2270-79.

Reinares, Pedro et al., "Fostering the process of adoption of personalized medicine: A matter of communication or a matter of cost?", Journal of Commercial Biotechnology, 2007, 13:199-207.

U.S. Appl. No. 12/910,165, NFOA—The unpredictability of the art, Graham Factors (p. 8-14).

* cited by examiner

$$300 \quad I_n = \begin{Bmatrix} D_{1,2} \\ D_{1,3} \\ D_{1,4} \\ D_{2,1} \\ D_{2,3} \\ D_{2,4} \\ D_{3,1} \\ D_{3,2} \\ D_{3,4} \\ D_{4,1} \\ D_{4,2} \\ D_{4,3} \end{Bmatrix}$$

FIGURE 4

$$G_{(x,y,x)} = \begin{Bmatrix} CYP2D6_{NM}, CYP2C9_{NM}, CYP2C19_{NM} \\ CYP2D6_{NM}, CYP2C9_{NM}, CYP2C19_{DM} \\ CYP2D6_{NM}, CYP2C9_{NM}, CYP2C19_{UM} \\ CYP2D6_{DM}, CYP2C9_{NM}, CYP2C19_{NM} \\ CYP2D6_{DM}, CYP2C9_{NM}, CYP2C19_{DM} \\ CYP2D6_{DM}, CYP2C9_{NM}, CYP2C19_{UM} \\ CYP2D6_{UM}, CYP2C9_{NM}, CYP2C19_{NM} \\ CYP2D6_{UM}, CYP2C9_{NM}, CYP2C19_{DM} \\ CYP2D6_{UM}, CYP2C9_{NM}, CYP2C19_{UM} \\ CYP2D6_{NM}, CYP2C9_{IM}, CYP2C19_{NM} \\ CYP2D6_{NM}, CYP2C9_{IM}, CYP2C19_{DM} \\ CYP2D6_{NM}, CYP2C9_{IM}, CYP2C19_{UM} \\ CYP2D6_{DM}, CYP2C9_{IM}, CYP2C19_{NM} \\ CYP2D6_{DM}, CYP2C9_{IM}, CYP2C19_{DM} \\ CYP2D6_{DM}, CYP2C9_{IM}, CYP2C19_{UM} \\ CYP2D6_{UM}, CYP2C9_{IM}, CYP2C19_{NM} \\ CYP2D6_{UM}, CYP2C9_{IM}, CYP2C19_{DM} \\ CYP2D6_{UM}, CYP2C9_{IM}, CYP2C19_{UM} \\ CYP2D6_{NM}, CYP2C9_{PM}, CYP2C19_{NM} \\ CYP2D6_{NM}, CYP2C9_{PM}, CYP2C19_{DM} \\ CYP2D6_{NM}, CYP2C9_{PM}, CYP2C19_{UM} \\ CYP2D6_{DM}, CYP2C9_{PM}, CYP2C19_{NM} \\ CYP2D6_{DM}, CYP2C9_{PM}, CYP2C19_{DM} \\ CYP2D6_{DM}, CYP2C9_{PM}, CYP2C19_{UM} \\ CYP2D6_{UM}, CYP2C9_{PM}, CYP2C19_{NM} \\ CYP2D6_{UM}, CYP2C9_{PM}, CYP2C19_{DM} \\ CYP2D6_{UM}, CYP2C9_{PM}, CYP2C19_{UM} \end{Bmatrix}$$

$$C_{D,G} = \begin{Bmatrix} 0, G_1 \\ 2, G_2 \\ 0, G_3 \\ 0, G_4 \\ 0, G_5 \\ 0, G_6 \\ 0, G_7 \\ 0, G_8 \\ 0, G_9 \\ 0, G_{10} \\ 0, G_{11} \\ 1, G_{12} \\ 0, G_{13} \\ 0, G_{14} \\ 0, G_{15} \\ 0, G_{16} \\ 0, G_{17} \\ 0, G_{18} \\ 0, G_{19} \\ 0, G_{20} \\ 2, G_{21} \\ 0, G_{22} \\ 0, G_{23} \\ 0, G_{24} \\ 0, G_{25} \\ 0, G_{26} \\ 0, G_{27} \end{Bmatrix}$$

$$P_G = \begin{Bmatrix} P_1 \\ P_2 \\ P_3 \\ P_4 \\ P_5 \\ P_6 \\ P_7 \\ P_8 \\ P_9 \\ P_{10} \\ P_{11} \\ P_{12} \\ P_{13} \\ P_{14} \\ P_{15} \\ P_{16} \\ P_{17} \\ P_{18} \\ P_{19} \\ P_{20} \\ P_{21} \\ P_{22} \\ P_{23} \\ P_{24} \\ P_{25} \\ P_{26} \\ P_{27} \end{Bmatrix}$$

| PATIENTS FOR WHOM CYP GENETIC TESTING IS RECOMMENDED | | |
|---|---|---|
| PATIENT | ◆ RISK PROBABILITY | EVIDENCE |
| PATTERSON, STELLA | 60% | ★★★★ |
| KEEGERSON, JACK (PROBLEM) | 35% | ★★★★ |
| BEACHUM, VERN (SOLDIER) | 35% | ★★★★ |
| THORNE, JACKSON | 57% | ★★★ |

FIGURE 13

SYSTEMS AND METHODS FOR QUANTIFICATION AND PRESENTATION OF MEDICAL RISK ARISING FROM UNKNOWN FACTORS

CROSS-REFERENCE TO RELATED APPLICATIONS

This application is a continuation of U.S. Non-provisional application Ser. No. 14/170,367, filed Jan. 31, 2014, which claims the benefit under 35 U.S.C. § 119(e) of U.S. Provisional Application 61/760,162, filed Feb. 3, 2013 and U.S. Provisional Application 61/771,850, filed Mar. 2, 2013. The afore-mentioned applications are incorporated herein by reference, in their entirety, for any purpose.

BACKGROUND

As the pharmaceutical industry advances, numerous drugs are available to address a variety of medical conditions. Individuals may increasingly be prescribed numerous drugs by multiple practitioners. Negative interactions between different drugs are a risk to patients that has been known for many years. Publications of known interactions and software tools that monitor medication lists assist medical care providers in preventing patients from receiving incompatible drug combinations. More recently, genetic research has shown that medications may react differently in patients with different genetic variants. It is estimated that 20-90% of an individual's variation to drug response is based on genetics. (Kang J. Testing Pathway-Dose Interaction in Clinical Studies. 2013 Joint Statistical Meeting—American Statistical Association.) Within the top 200 selling prescription drugs, 59% of the 27 most frequently cited in adverse reactions are metabolized by at least one enzyme known to have gene variants that code for reduced-functioning or non-functioning proteins. (Phillips K A, Veenstra DL, Oren E, Lee J K, Sadee W. Potential Role of Pharmacogenomics in Reducing Adverse Drug Reactions: A Systematic Review. JAMA. 2001; 286(18):2270-2279.)

Patients with different drug metabolizing enzyme phenotypes based on their genotype may metabolize drugs at different rates. More than 75% of the population has genetic variations that decrease or increase the availability or characteristics of cytochrome enzymes used in drug metabolism. For example, three cytochrome P450 enzymes, CYP2D6, CYP2C9, and CYP2C19 process more than 50% of all medications routinely prescribed. If a patient has a genetic variation affecting the availability of one of these enzymes and is prescribed a drug that relies upon one of those enzymes, an adverse drug event of overdose toxicity or treatment failure may occur. For example, if a patient has lower CYP2C9 enzyme levels, the patient may metabolize warfarin more slowly. This could lead to the patient suffering symptoms of overdose toxicity at a dosage within the normally prescribed therapeutic range. This may require adjusting the dose of the medication or choosing a different medication for the patient to prevent an adverse drug event.

Although increasing amounts of information on pharmacogenetic effects is available, it is still cost prohibitive to obtain genotype information for every individual patient. Often, healthcare providers have limited, if any, information about the genotype of their patients.

Moreover, testing to identify particular patient genotype information by DNA testing—may be costly. Healthcare providers are generally without tools which allow them to easily assess when, and in what patient populations, the costs of obtaining genotype information may outweigh potential adverse outcomes.

BRIEF DESCRIPTION OF THE DRAWINGS

FIG. 3 is an example matrix $\{D_i\}$ of medications in accordance with examples described herein.

FIG. 4 is an example matrix $\{I_n\}$ of drug-drug interactions in accordance with examples described herein.

FIG. 5 is an example matrix $\{G(x,y,z)\}$ of phenotypes in accordance with examples described herein.

FIG. 6 is an example matrix $\{C_{D,G}\}$ of drug-gene interactions in accordance with examples described herein.

FIG. 7 is an example matrix $\{P_G\}$ of probabilities of phenotypes in accordance with examples described herein.

FIG. 13 is an example individual list in accordance with an embodiment of the invention.

DETAILED DESCRIPTION

Although the following detailed description contains specific details for the purpose of providing a thorough understanding of the subject matter, one of ordinary skill in the art will appreciate that many variations and alterations to the following details are within the scope of the invention. Accordingly, the invention should not be limited to the embodiments and examples described below.

Some portions of the detailed description that follows are presented in terms of algorithms, programs, and/or symbolic representations of operations on data or data bits within a computer memory, for example. These algorithmic descriptions and/or representations may include techniques used in the data processing arts to convey the arrangement of a computer system and/or other information handling system of operation according to such programs, algorithms, and/or symbolic representations of operations.

Embodiments of systems and methods described herein may aid a user (e.g. a patient, a healthcare provider, an insurer, a healthcare practice, a healthcare facility, or another computer process) in managing adverse drug event risk associated with their treatment. Many examples provided herein relate to managing risk associated with drug selection and dosing. However, in other examples, examples utilizing the methods and systems described herein may instead manage risk associated with other treatments—e.g. surgical cardiac treatments. Generally, examples of methods and systems described herein develop a quantification of a known risk of an event (e.g. an adverse drug interaction that changes the metabolism of a drug and leads to suboptimal blood levels of the drug) and further develop a quantification of the unknown risk of that event. In this manner, review of the quantification of the unknown risk, in some examples relative to the known risk, may allow decision makers to realize when it may be advantageous to gather additional information (e.g. genetic testing to determine patient drug metabolizing capacity or, liver and kidney function testing, EKGs, and other tests to monitor for the existence of an asymptomatic ADE).

Figure 1:
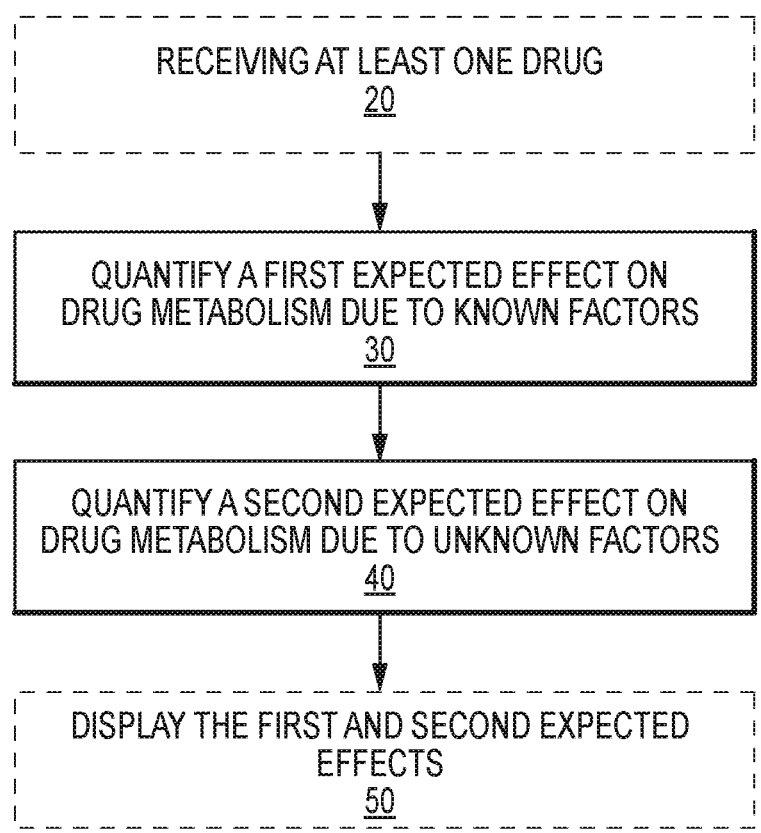
FIG. 1 is a schematic illustration of a method arranged in accordance with examples described herein.

FIG. 1 is a schematic illustration of a method arranged in accordance with examples described herein. In the example method 10 of FIG. 1, expected effects on drug metabolism may be quantified. A computing system may receive identification of at least one drug 20. The computing system may quantify 30 a first expected effect on metabolism of the drug by a patient due to known factors and may additionally or instead quantify 40 a second expected effect on metabolism of the drug by the patient due in part to unknown factors. The first and second expected effects may be displayed 50.

As shown in element 20, example computing systems may receive identification of at least one drug. Any number of drugs may be received by the computing system. Generally, the drugs received may correspond to a current drug regimen of a patient. In some examples, the drugs may include drugs which are being considered for use by the patient and/or were previously used by the patient. By drugs, herein is meant a substance that may be ingested by the patient for medical use. Drugs include, but are not limited to, painkillers, cardiac medications, beta blockers, antihistamines, anti-inflammatories, narcotics. Generally, anything which may be prescribed may be used as a drug as described herein. In some examples, drugs may refer to other substances, including, but not limited to, dietary supplements, herbs, vitamins, foods or combinations thereof.

Any number of drugs may be provided, including but not limited to 1, 2, 4, 5, 6, 7, 8, 9, or 10 drugs. More drugs may be provided in other examples. In some examples, the drugs may be provided by entering the drugs into a computing system which may be in communication with the computing system configured to perform the quantification methods described herein. In some examples, the drugs may be entered into the computing system used to perform the quantification directly. In some examples, the drugs are received and stored. Storage may not be necessary in other examples.

As shown in element 30, a computing system may quantify a first expected effect on drug metabolism due to known factors. Generally, a factor refers to something which affects the metabolism of a drug by an individual. Examples of factors include, but are not limited to, genotype, phenotype, liver function, kidney function, weight, age, ethnicity, and combinations thereof. Some factors may be known for a particular individual and others may be unknown at the time the quantifications are made.

Depending on the identity of factors for an individual, the risk of an adverse drug event may be increased or decreased. For example, an individual with normal genetics and excellent liver function may have a lower risk of suffering from an adverse drug event than an individual with different genetics and/or poor liver function. Known factors may include factors that are published in medical literature that are independent of the individual. For example, previous research may show that two drugs interact negatively when prescribed together (e.g., a drug-drug interaction), regardless of the individual to whom they are prescribed. Other factors may be known from information collected from the individual. For example, a medical care provider may have conducted kidney function tests or genetic tests to determine the kidney function of an individual or a particular genotype of the individual. Once a factor is known, an expected effect on drug metabolism due to that known factor may be calculated.

In some cases, however, there may be factors which may affect the metabolism of a drug, but the identity of the factor may be unknown for an individual. For example, it may be that the presence of a particular genotype affects metabolism of a particular drug. However, the genotype of an individual may be unknown. Accordingly, there is an unknown risk of the individual's drug metabolism being affected by the factor. Some unknown factors may become known by conducting additional medical tests. Others may not be discoverable without further scientific research. For example, additional genetic variants that affect drug metabolism may be discovered in the future. Unknown factors contribute to an individual's unknown risk for experiencing an adverse drug event. Some of this unknown risk may be reduced by collecting additional information, but some unknown risk may not be able to be eliminated. In some cases, the probability that an unknown factor has a particular identity may be known. For example, it may be unknown whether an individual has a particular genotype which effects metabolism of a drug, however, the prevalence of that genotype in the population may be known. In some examples, the probability of the unknown factor having a particular identity may be used to quantify the risk of an outcome (e.g. effect on drug metabolism).

Factors which may affect drug metabolism may include the phenotype of one or more cytochrome P450s (CYP). Cytochromes are enzymes that assist in chemical reactions involved in metabolism. For example, cytochromes and other proteins may assist in constructing, transporting, breaking down and eliminating different chemicals in the body. The series of chemical reactions that a drug or chemical undergoes in the body may be referred to as a metabolic pathway or route. One or more cytochromes or other proteins may be part of the metabolic pathway of a drug. Other factors include glucuronosyltransferases (UGT) enzymes which perform glucurodination reactions, and transporters which are proteins that regulate the movement of substances across membranes. Variations in the structure or prevalence of the proteins may affect the way drugs or other chemicals are processed by the body. These variations in the metabolism of a drug may cause an individual to react differently to the drug. For example, if an individual metabolizes a drug more slowly than expected, the drug may increase in concentration in the blood stream of the individual and cause toxic effects. If on the other hand the individual metabolizes the drug more rapidly their blood level may not be sufficient for the drug to have a therapeutic effect.

Variations in cytochrome performance across individuals may be explained in some cases by differences in the individuals' genotypes. The genotype is the genetic code of the individual for a trait or characteristic. Examples of traits include the structure of a particular protein, eye color, and blood type.

Phenotypes may also be factors in examples described herein. Phenotypes generally refer to observable traits based on the genotype. Two individuals possessing the same genotype for a cytochrome of interest may have the same structure and prevalence of the cytochrome. However, other individuals with different genotypes may also present the same structure and prevalence of the cytochrome as well. Although the genotypes of the other individuals are different, the individuals may belong to the same phenotype for the cytochrome of interest. Differences in phenotype or genotype that result in an adverse drug event are considered drug-gene interactions.

Quantifying the known and unknown risks of an individual based on known and unknown factors (e.g. in elements 30 and 40 of FIG. 1) generally involves generating a numerical representation of risk. Multiple methods may be used to quantify known and unknown risks. For example, the number of known interactions (e.g. drug-drug interactions) may be compared to the number of possible interactions for an individual for whom certain factors (e.g. geneotype) is unknown. So, in some examples, quantifying refers to developing a count of a number of possible interactions. In some examples, a method may weight different factors differently rather than a simple comparison of quantity of interactions. For example, the severity of clinical outcome of an interaction may be considered. A mild effect may be defined as something that causes discomfort, but not lasting harm to the individual. For example, a headache or upset stomach. A severe effect may be defined as something potentially life-threatening such as internal bleeding or organ shutdown. The classification of severity of interactions may vary in different embodiments. As an example of weighting risk based on severity, if an individual's liver function is unknown, but the drug of interest does not have a significant change in clinical effect based on liver function, that unknown risk may be weighted less heavily than a factor with a more severe effect. A method may alternatively or additionally take probability of an unknown risk into consideration in quantifying risk. For example, the different phenotypes of a cytochrome may have different prevalence in the population. Accordingly, the unknown risk of an adverse drug-gene interaction may be weighted based on the probability of an individual possessing a particular phenotype. Each unknown risk may be compared to a known risk individually or a cumulative value of unknown risk for all the unknown factors may be computed for comparison against a cumulative value of known risk.

In some embodiments, the presence of a drug-gene interaction may be quantified (e.g. calculated) by computing the effect of exposure of an individual to a drug. For example, the blood concentration over time of the drug in an individual may be calculated. Drugs may have a pre-defined therapeutic range, that is, a range of concentration in the blood that provides a therapeutic effect. Concentrations outside this range may fail to provide a therapeutic effect or may cause a toxic effect in the individual. The concentration over time for a drug may be computed for each factor and for one or more metabolic routes used in metabolism of the drug. For example, if a particular cytochrome phenotype variation is known to increase the metabolism of a drug, this factor is used to calculate a prediction of the concentration over time of the drug. If this increase in metabolism of the drug causes the concentration over time to fall outside the therapeutic range, a drug-gene interaction may be determined to exist for that drug/phenotype combination. As discussed above, the drug-gene interaction may be simply counted, summed with other risk factors relating to a particular drug, and/or weighed based on the severity of the resulting drug-gene interaction.

Examples of methods used to calculate predictions of drug concentrations are described, for example, in U.S. Pat. Nos. 8,099,928 and 8,311,851, both of which are hereby incorporated by reference in their entirety, for any purpose. In some examples, if a drug concentration is predicted to be above or below a threshold or range, it may be considered an adverse drug interaction. Examples of methods used to calculate a drug concentration include identifying metabolic routes used to metabolize a drug. For each metabolic route and factor, a predicted effect on drug metabolism may be summed. In this manner, cumulative effects on drug metabolism may be taken into consideration—e.g. effects arising from a drug-drug-gene interaction. By summing effects on metabolism that arise from multiple factors affecting a pathway, cumulative effects may be considered beyond just an effect of a single factor.

Examples described herein include computing systems and methods that display quantified effects due to known and/or unknown factors. A user, such as a medical care provider, may observe these effects, which may reflect known and unknown risk, and use the quantified effects to make decisions such as order additional medical tests and/or alter the drugs prescribed to the individual. As more information becomes known and/or changes are made based on the quantification, a user may be able to track their increase or reduction of known and unknown risks over time. This may allow users to evaluate the effectiveness of clinical practices at reducing risk of individuals.

Example data structures are described herein which may facilitate quantification by computing systems. To quantify expected effects due to multiple and complex factors, computational load may become quite large. Examples described herein may employ data structures and techniques which may allow for quantifying expected effects due to known and/or unknown factors in an amount of time that may be acceptable for a user to be able to review risks in a practical time frame. Examples described herein may refer to the factors and interactions stored in matrices for use by a quantification system. A matrix generally refers to a rectangular array of numbers or symbols arranged in rows and columns. Matrices may be stored in electronic memory in substantially any form or data structure, and are not restricted to a particular physical layout. A first matrix may contain drugs known to be used by an individual. A second matrix may contain drugs for which interactions with other drugs are known. The two matrices may be compared by the quantification system to generate a third matrix that contains drug interactions that pertain to the drugs the individual is known to use the drugs in the first matrix). Other data such as phenotype prevalence in a population (which may be stored as a probability) or a numerical measure of clinical severity of an interaction may also be stored in matrices. In other embodiments, factors and other data may be stored in different structures for use.

Figure 2:
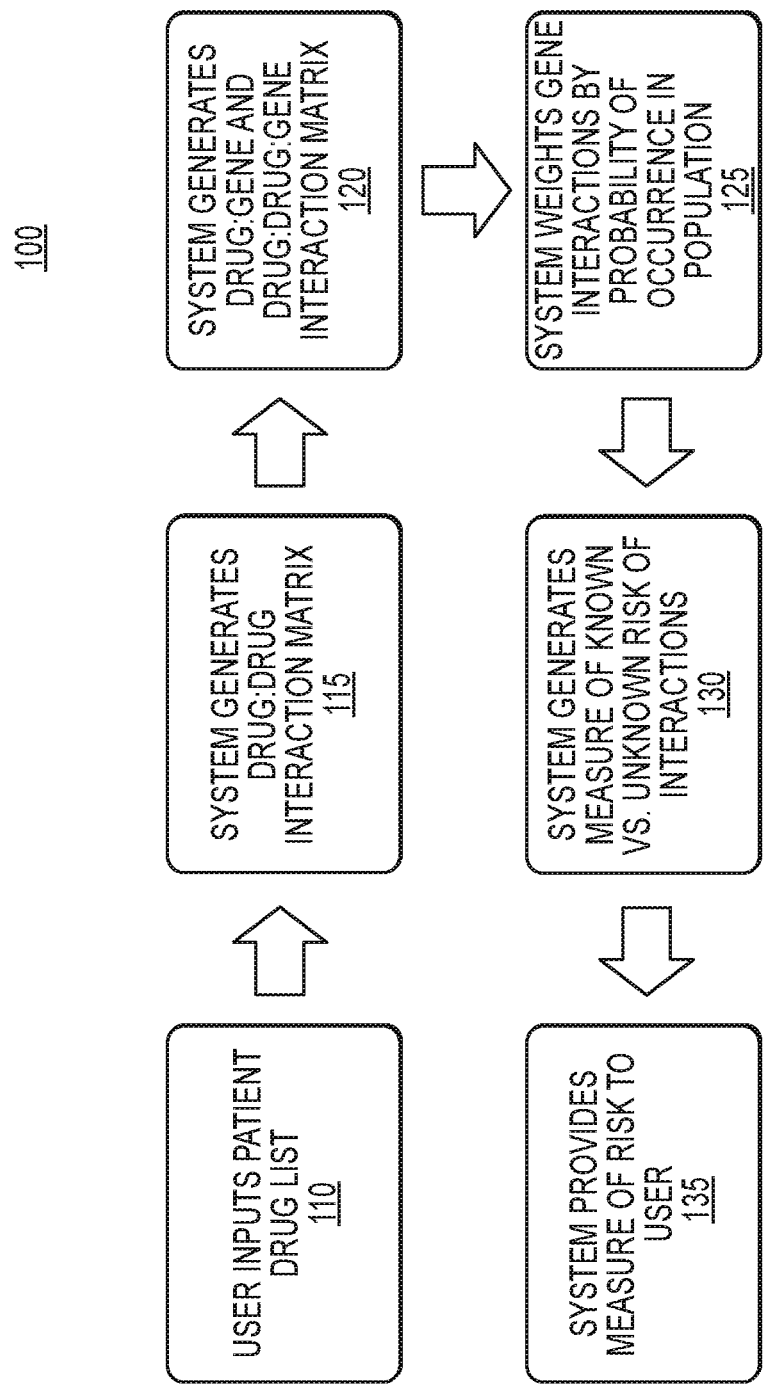
FIG. 2 is a flow chart of an example method for calculating an individual's risk of an adverse drug event according to an embodiment of the invention.

FIG. 2 is a flow chart of an example method for calculating an individual's risk of an adverse drug event according to an embodiment of the invention. At 110, a user, such as a medical provider, may input drugs an individual is known to use, and/or the medical provider is considering prescribing, into a risk quantification system. In other examples, the drug list may additionally or instead be stored in the system and may not be input as part of the method. The system may use the input to generate a matrix of known drugs used by the individual. A matrix of known drug interactions may be stored in a memory or other storage device accessible to the system or included in the system and may be compared to the matrix of known drugs used by e individual to generate a matrix of drug-drug interactions at 115.

A matrix of known possible phenotype variations in a population may be stored in a memory or other electronic storage accessible to the system, which may or may not be the same as the memory used to store the drug matrices described herein. Other factors such as genotype or liver function may be used alternatively or in addition to phenotype. The matrix of known drugs and the matrix of known possible phenotype variations may be compared to produce a matrix of known drug-gene and drug-drug-gene interactions at 120. Although the determination of drug-drug interactions is shown as occurring before the determination of drug-gene interactions in this example, the determinations may occur in reverse order or parallel. A matrix of the probabilities of the possible phenotype variations may also be stored in a memory or other storage accessible to the system. The probability of possible phenotype variations may be based on studies of phenotype prevalence in populations. The matrix of the probabilities of possible phenotype variations may be multiplied with the matrix of known drug-gene and drug-drug-gene interactions to produce a probability that the individual may suffer an adverse drug event at 125. The system may then compare the drug-drug interactions, e.g. the known risk, to the probability of the drug-gene and drug-drug-gene interactions, e.g. the unknown risk at 130 to generate a measure of patient risk. Data on the severity of the interactions may be stored in a memory or other location accessible to the system and may optionally be used to weight the risk calculation. The result generated at 130 may then be provided to the user numerically and/or graphically at 135. Those individuals for whom the system computes a high unknown risk of an adverse drug event (e.g. over a threshold) may most benefit from having more detailed genetic testing completed to determine an actual drug interaction.

Example matrices used to carry out the method shown in FIG. 2 will now be described. The matrices are shown by way of example, and the data shown in the matrices may be arranged in other data structures in other examples. Element 110 recites inputting a drug list. The drugs entered may be all the drugs currently being consumed by a patient, and may also include herbals, over-the-counter medications, and pharmacoactive food substances, such as grapefruit. A matrix {Di} of medications may be constructed and may be stored in a memory or other storage location accessible to the system. An example matrix {Di} 200 is shown in FIG. 3. In this example, four drugs have been entered, but more or fewer drugs may be entered in other examples. The calculation then proceeds by providing possible binary interactions in a second matrix {In}. An example matrix {In} 300 is shown in FIG. 4. The matrix {In} 300 is generated based on the matrix {Di} 200. The matrix {In}, shown in FIG. 4, represents possible drug-drug interactions. All binary combinations of drugs listed in the matrix {Di} are represented in the matrix {In}. Since there were 4 drugs in the matrix {Di}, there are then 12 combinations listed in the matrix {In}. Each combination may be evaluated to determine if the combination may produce a drug-drug interaction.

The combinations listed in matrix {In} may be evaluated by comparing the combinations against stored known adverse drug-drug interactions. The store of known drug-drug interactions may include drug-drug interactions reported in medical or other literature, publicized by a pharmaceutical company or other source, or calculated by the system. For example, the matrix {In} may be compared against a matrix stored in a memory accessible to the system containing known drug interactions. Combinations that do not correspond to known interactions may be removed from the matrix {In}. Optionally the matrix {In} 300 may be further filtered by removing mild interactions or those known to result in little or no clinical effect. The severity of reactions may similarly be stored in a memory or other location accessible to the system, which may facilitate filtering. In this manner, the matrix {In} may be reduced in size to leave only those drug-drug interactions causing an adverse event, or a significant adverse event in some examples.

To evaluate drug-gene interactions where genetic information (and therefore cytochrome phenotype) may not be known, probability estimations of the prevalence of the phenotype variations may be used. Each evaluation may involve multiple iterations based on probability factors for each possible substituent of a matrix.

FIG. 5 is a schematic representation of an example of a matrix {G(x,y,z)} 400 of 27 possible phenotypes, each row including one compound phenotype having as attributes three phenotypes, one for each of three cytochromes, CYP2D6, CYP2C9, and CYP2C19. Although CYP2D6, CYP2C9, and CYP2C19 are used in this example, additional or different cytochromes may be used in other examples, such as CYP3A4 and CYP3A5, or other factors in other examples. Other factors may include organ function, weight, pregnancy, or combinations thereof.

Matrix {G(x,y,z)} 400 of phenotypes may be used in one or more embodiments of the invention. This matrix may be stored in a memory accessible to the system and used at 120 in FIG. 2. The example matrix {G(x,y,z)} 400 may be formed by genetic variants of three Cytochrome P450 enzymes. Here CYP2D6, CYP2C9 and CYP2C19 are considered, but other enzymes may be considered. Each row corresponds to a particular allelic combination, the combined phenotype represented by three cytochrome loci taken in combination. An allele generally refers to one of two or more forms of a gene that is located at the same place on a chromosome. In this example, IM (intermediate metabolizer) represents a heterozygous condition, and that PM (poor metabolizer) and NM (normal metabolizer) are generally homozygous. Ultra (UM) and rapid (RM) metabolizer phenotypes are also shown.

Those skilled in the art will appreciate the extra levels of complexity involved in phenotyping allelic pairs where the alleles are mixed. These complexities are not considered here so as to avoid overburdening the explanation. The principles of the calculation suffice for working with a matrix having thousands of allelic pair combinations for the three loci or for three hundred loci. Parallel processing techniques may be used to reduce computation time. Data masking may also be used to reduce computation time by focusing on the most relevant data.

FIG. 5 simplifies the number of possible phenotypes to 27 by combining selected phenotypes. Ultra- and rapid metabolizer are combined as "UM". Poor and intermediate metabolizer are combined as "DM". This is done to simplify the subsequent explanation, and is not intended as a limitation on the invention. A fewer or greater number of phenotypes may be used in other examples. As shown in FIG. 5, each of the cytochromes may have three possible phenotypes. CYP2D6 may have the NM, UM, and DM phenotypes—each of which may reflect a different level of metabolism by the cytochrome. CYP2C9 may have three possible phenotypes, NM, IM, and PM. CYP2C19 may have three possible phenotypes—NM, UM, and DM. Listing all possible combinations of the three yields the 27-line matrix in FIG. 5. Generally, the matrix G shown in FIG. 5 may have a size equal to the product of the number of possible phenotypes for each cytochrome. In the case of FIG. 5, since there are three cytochromes with three possible phenotypes each, the size is 3×3×3=27. If one cytochrome had 2 possible states, the size would instead be 3×2×3=18. In more complex embodiments, the genotype itself, expressed for each allelic pair, and including copy number variation, can be formed into like arrays for purposes of making detailed computations. While it is convenient to use phenotype, it is understood that either the phenotype or the underlying alleles/genotype may be used by example systems to make risk calculations and to suggest alternatives to medical decision makers.

Matrix $\{G(x,y,z)\}$ 400 may be combined with matrix $\{Di\}$ 200 and/or matrix $\{In\}$ to form a matrix of drug-gene and drug-drug-gene interactions at 120 in FIG. 2. The shorthand $G_2$, $G_4$, $G_{10}$ is used to represent rows of particular phenotype combinations from FIG. 5. The matrix of possible drug-gene and drug-drug-gene interactions may be compared against a matrix accessible to the system of known drug-gene interactions. Alternatively, or in addition, adverse drug events (e.g. drug-gene or drug-drug-gene) interactions may be determined by the system by a computing system utilizing an algorithm to calculate the expected effect on metabolism of a drug due to one or more factors (e.g. genotype, phenotype, etc.). The computing system may quantify the expected effect on metabolism for each drug for each metabolic pathway involved in the drug's metabolism for the different combinations of possible factors (e.g. phenotypes). The computing system may then sum the results for each metabolic pathway. If for a given phenotype combination, the effect on metabolism causes the amount of drug to fall outside a specified range (e.g. a therapeutic range), an adverse drug event (e.g, a drug-gene or a drug-drug-gene interaction) is considered to occur. Examples of suitable algorithms are described, for example, in U.S. Pat. No. 8,311,851, which is hereby incorporated by reference in its entirety for any purpose. Combinations (e.g. drug/phenotype combinations) that do not correspond to a known interaction may be removed from the drug-gene interaction matrix. An example drug-gene interaction matrix $\{C_{D,G}\}$ 500 is shown in FIG. 6. Optionally the matrix $\{C_{D,G}\}$ 500 may be further filtered by removing more mild interactions or those known to result in little or no clinical effect. The drug-gene interaction matrix $\{C_{D,G}\}$ lists the number of interactions for each gene combination considered in matrix $\{G(x,y,z)\}$ 400. However, using the examples of FIGS. 2-5, as many as 12*27 drug-drug gene interactions may be present (e.g. the 12 drug-drug interactions of matrix $\{In\}$ multiplied by the 27 possible relevant genotypes of the matrix G). The matrix C may further include 27×4 drug-gene interactions. Generally, then the size of matrix C may be equal to the number of possible phenotypes multiplied by the number of drug-drug interactions plus the number of possible phenotypes multiplied by the number of drugs. As shown in FIG. 6, only six possible significant reactions remained after the system removed those which were not known or calculated to cause an adverse effect. The system may store which drugs interact with each gene combination in a separate matrix or other data structure (not shown).

FIG. 7 illustrates an example matrix $\{P_6\}$ 600 that includes the probabilities of each phenotype combination contained in matrix $\{G(x,y,z)\}$ 400. Matrix $\{P_G\}$ 600 may be stored in a memory accessible to the system. Matrix $\{P_G\}$ 600 is multiplied by matrix $\{C_{D,G}\}$ 500 at 125 in FIG. 2. Before the calculation, if matrix $\{C_{D,G}\}$ 500 has been reduced to only known interactions or only severe reactions, matrix $\{P_G\}$ 600 may also be reduced such that it contains only the probabilities for the phenotype combinations considered in matrix $\{C_{D,G}\}$ 500. The matrix $\{P_G\}$ 600 may be for the general population or may be for a specific subset (e.g. race, geographic group, gender) if such classifying information is known. For illustration, in a particular cohort, the overall prevalence of CYP2D6 poor metabolizers was 7.6%, (8.2% in European-Americans and 1.8% in African-Americans). The overall prevalence of CYP2D6 ultra-rapid metabolizers was 1.5%, (1.5% in European-Americans and 2.0% in African-Americans). The overall prevalence of CYP2C19 poor metabolizers was 2.0%, (2.2% in European-Americans and 4.0% in African-Americans). From this kind of data, additional probability matrices may be constructed according to ethnicity, geography, nationality, family association, and other indicators of genetic lineage. In some instances, linked markers indicative of genetic lineage may be used to select suitable matrices of genetic marker distribution frequencies.

Figure 8:
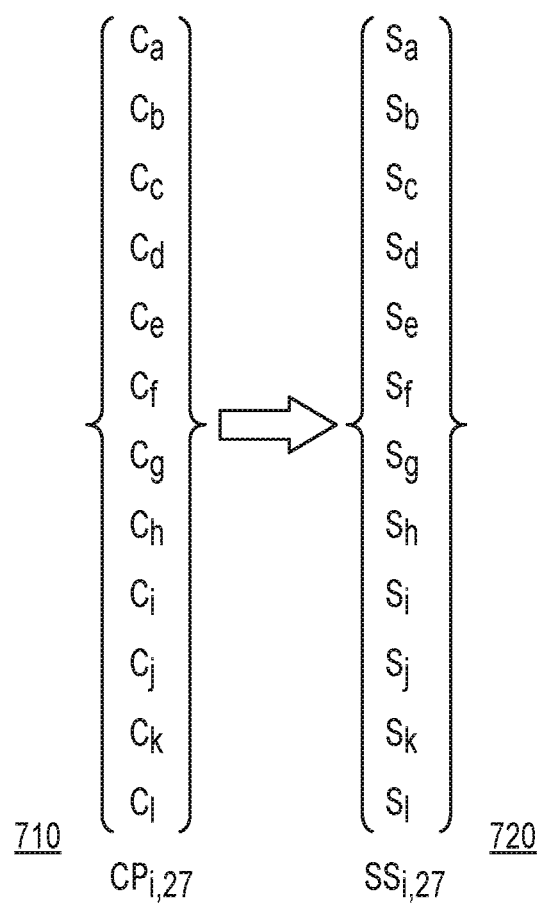
FIG. 8 illustrates operations on a series of matrices to generate data indicative of the severity and probability of adverse outcomes in accordance with examples described herein.

FIG. 8 shows how operations may be performed on a series of matrices to generate data indicative of the severity and probability of adverse outcomes. For simplicity, it will be assumed that the calculation involves the 27 alternative phenotypes as shown in FIG. 5, but different phenotype or gene combination sets may be used. From the multiplication of matrix $\{C_{D,G}\}$ 500 and $\{P_G\}$ 600, a new matrix $\{CP(i, 27)\}$ 710 may be generated. The set of interactions $\{CP(i, 27)\}$ 710 will generally include induction effects on metabolic enzymes, inhibition effects, fractional metabolism by multiple pathways, and the effect of genotypes for the 27 possible phenotypes in this example. From matrix $\{CP(i, 27)\}$ 710 possible changes, individual risk severity scores are assigned to each possible interaction. Each outcome CPi is scored according to presumptive clinical consequences, here for example a set of risk categories ranging from negligible to major are used, and the scored data is stored in a "set-of-scores" matrix $\{SSi,27\}$ 720. Thus set SSi is a severity matrix having i by 27 members. Each member of the SS matrix is a possible outcome because the actual phenotype of the patient is unknown.

Combinations having severe outcomes may then be considered. If there is an outcome where there are three possible severe reactions, for example, and each reaction has a probability of 10 percent, then a total probability of 30% that there will be three severe adverse drug events given that medication list and the possible phenotypes that cannot be ruled out. This is a level of unknown risk since genetic information for the individual is unknown.

The system may compare the total count of drug-drug interactions evident in a drug list versus the total count of drug-gene reactions apparent given genetic data at 130 in FIG. 2. If the number and/or severity of drug-drug interactions is equal to the projected drug-drug-gene interaction count, then genetics may not be a factor in the particular drug list under consideration. However, if the two scores differ, then genetics may play a role in the risk of the individual.

Figure 9:
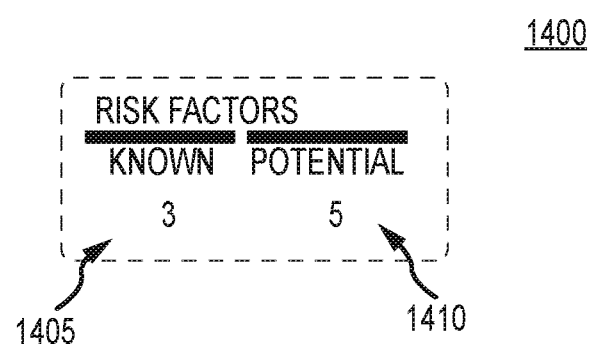
FIG. 9 illustrates a risk factor count in accordance with examples described herein.

The system may display the measure of known and unknown risk at 135 in FIG. 2 in a number of ways. In some embodiments, the system is intended to stimulate use of genetic testing in risk reduction strategies by individual decision makers and healthcare institutions, so it can be structured to compare the risks associated with particular medication lists with versus without genetic testing. The system may return two numbers and the difference between the numbers will be indicative of the number of unknown risks associated with lack of genetic testing data for the individual. FIG. 9 illustrates an example risk factor count 1400 determined by the system in accordance with an embodiment of the invention. The number of known reactions 1405 is three, and the unknown, or potential reactions 1410 is five. The number of known reactions 1405 may be the number of drug interactions found in matrix 300. The number of known reactions 1405 may also include known drug-gene and/or drug-drug-gene interactions if such information is available for the individual. The number of potential reactions 1410 includes the total number of potential reactions determined at 120 in FIG. 1. This may include the interactions calculated in matrix $\{C_{D,G}\}$ 500. The number shown for potential reactions 1410 may be the "worst case scenario," that is, the greatest number of potential reactions for the individual. In other embodiments, the potential reactions 1410 may be the most probable number of reactions based on the probability calculation at 125 in FIG. 1. The system may provide only a count of potential severe interactions as weighted by matrix $\{SSi,27\}$ 720 in some examples. The value used for potential reactions 1410 may be modified based on user preference. In this example, the unknown interaction count is greater than the known interaction count, and additional testing may be advised to reduce the unknown risk.

Figure 10:
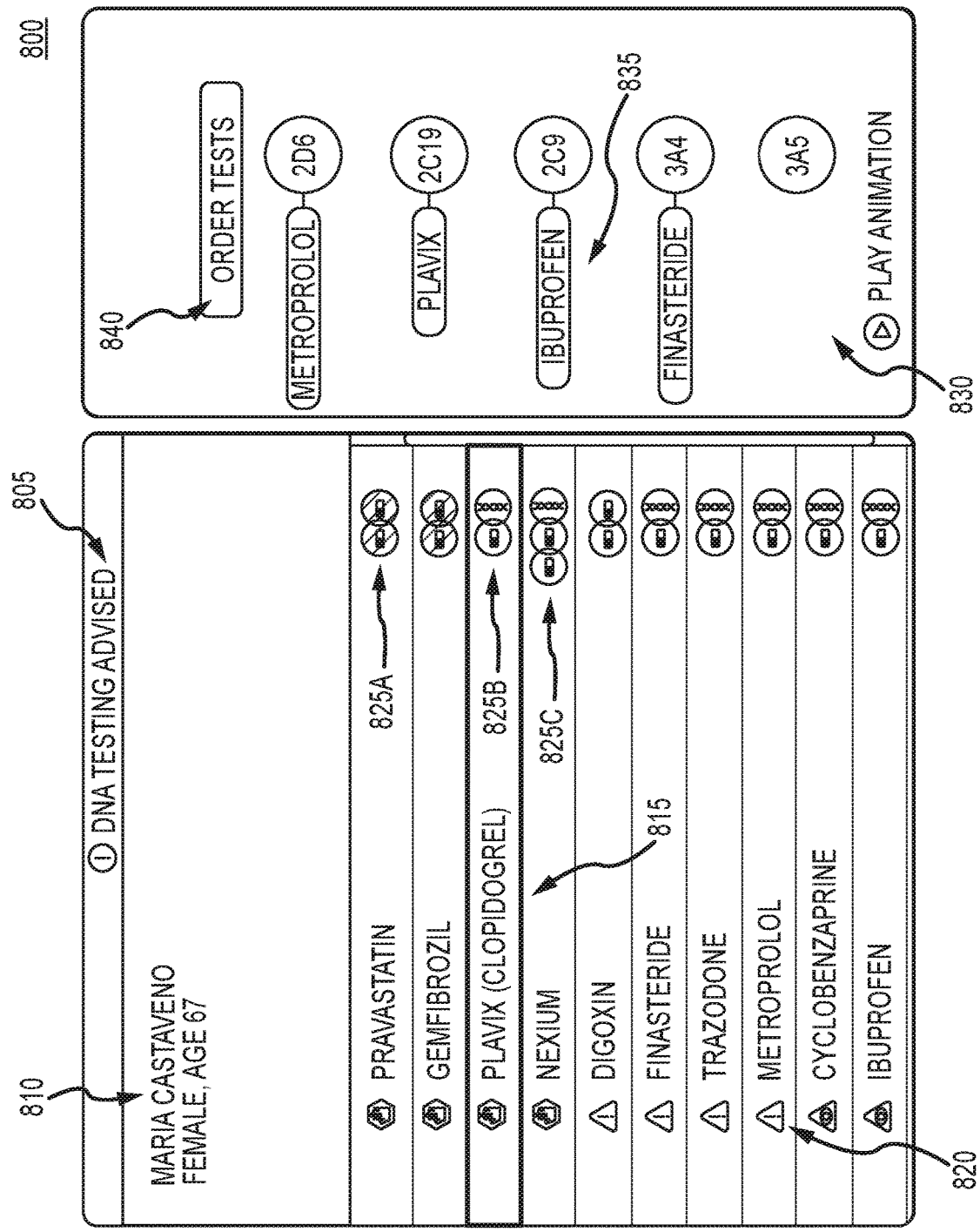
FIG. 10 illustrates an interaction report before genetic testing in accordance with an embodiment of the invention.

An example method of displaying the measure of risk in accordance with an embodiment of the invention is shown in FIG. 10. The system displays the measure of risk in the form of an interaction report 800. Interaction reports may be tailored to suit particular clinical practices. It will also be readily appreciated that the reports can include additional elements or modified elements. For example, where electronic, the report can contain hyperlinks which point to internal or external databases which provide more detailed information about selected elements of the report. For example, the genetic test platform report element can include a hyperlink to a website of the manufacturer of the genetic test platform. The patient data element of the report can include a hyperlink to an electronic patient record, or a site for accessing such a patient record, which patient record is maintained in a confidential database. The patient record may contain information on the patient's health status such as disease state, renal function, pregnancy, and information on previously conducted medical tests. This latter embodiment may be of particular interest in an in-hospital system or -in-clinic setting.

The interaction report 800 includes a graphical indicator that genetic testing is advised by the system based on the measure of risk calculated. In the illustrated example, the graphical indicator is a status bar 805, but it could take other forms such as an icon in the patient information field 810. The patient information field 810 is displayed at the top of the interaction report 800. The patient information field may include patient name, patient age, gender, primary care physician, or other information relevant to the particular environment in which the system is used.

Below the patient information field 810 is the medication list 815. This medication list corresponds to the drugs and other substances entered into the system at 110 in FIG. 2, which may correspond to data that may be included in matrix $\{Di\}$ 200. To the left of each medication, a severity icon 820 appears. In this particular example, the severity icons are different shapes and colors, corresponding to different levels of severity of the interaction, wherein red correspond to the greatest severity, orange corresponds to medium severity, and yellow corresponds to low severity. Greater or fewer levels of severity may be implemented in the system, and different color or shape classification systems may be used. The severity icons may be assigned based on the information that may be contained in matrix SSi 720. To the right of each medication is an interaction icon 825. The interaction icon 825 displays the type of interaction determined by the system. These interactions may have been determined by the data that may be included in matrices $\{In\}$ 300 and $\{C_{D,G}\}$ 500. In the example illustrated, interlocking circles are used to show an interaction. Different graphics within the circle indicate a drug or a gene involved in the reaction. Different shape and graphic combinations may also be used. The interaction icon 825A corresponds to a drug-drug interaction; 825B is a drug-gene interaction; 825C is a drug-drug-gene interaction. The circles for the drug-drug interactions are filled in to indicate that these are known risks. The circles for the drug-gene risks are not filled in to indicate that these are unknown risks because the individual has not been genetically tested.

The interaction report 800 may optionally display a sidebar 830 that graphically displays a summary of the information provided in the medication list 815. The sidebar 830 may contain a variety of elements such as animations of drug metabolism through enzymatic pathways 835, and/or an option to order genetic tests for the individual 840. The graphics contained in the sidebar 830 may be customized to allow information relevant to a particular environment to be understood quickly by a user.

Figure 11:
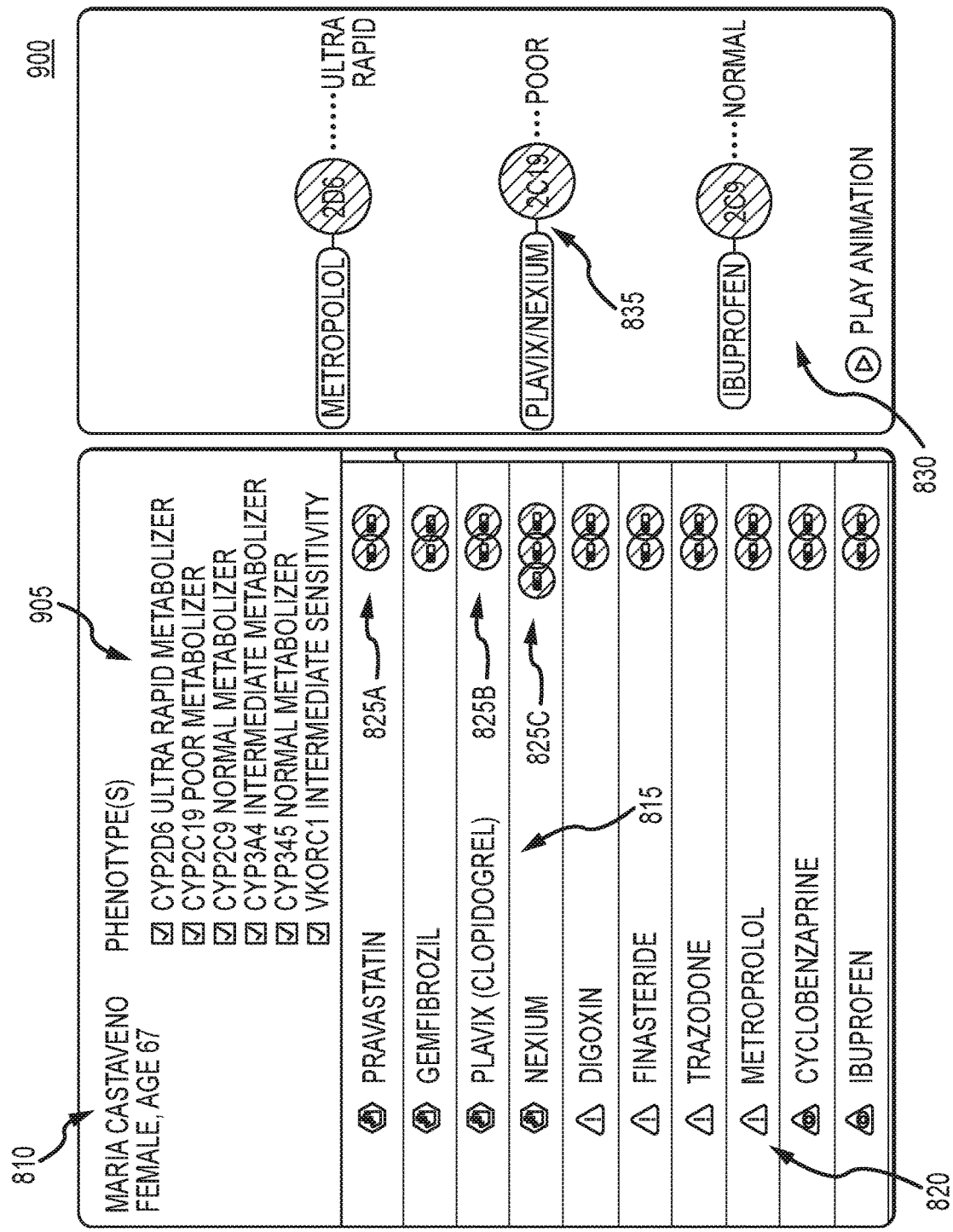
FIG. 11 illustrates an interaction report after genetic testing in accordance with an embodiment of the invention.

FIG. 11 illustrates an example interaction report after genetic testing has been completed 900. The patient information field 810 now contains the results of the genetic tests 905, and the medication list 810 is updated to display the relevant interactions based on the genetic test results. Note the circles for existing drug-gene risks are now filled in to indicate the risk is known.

Figure 12:
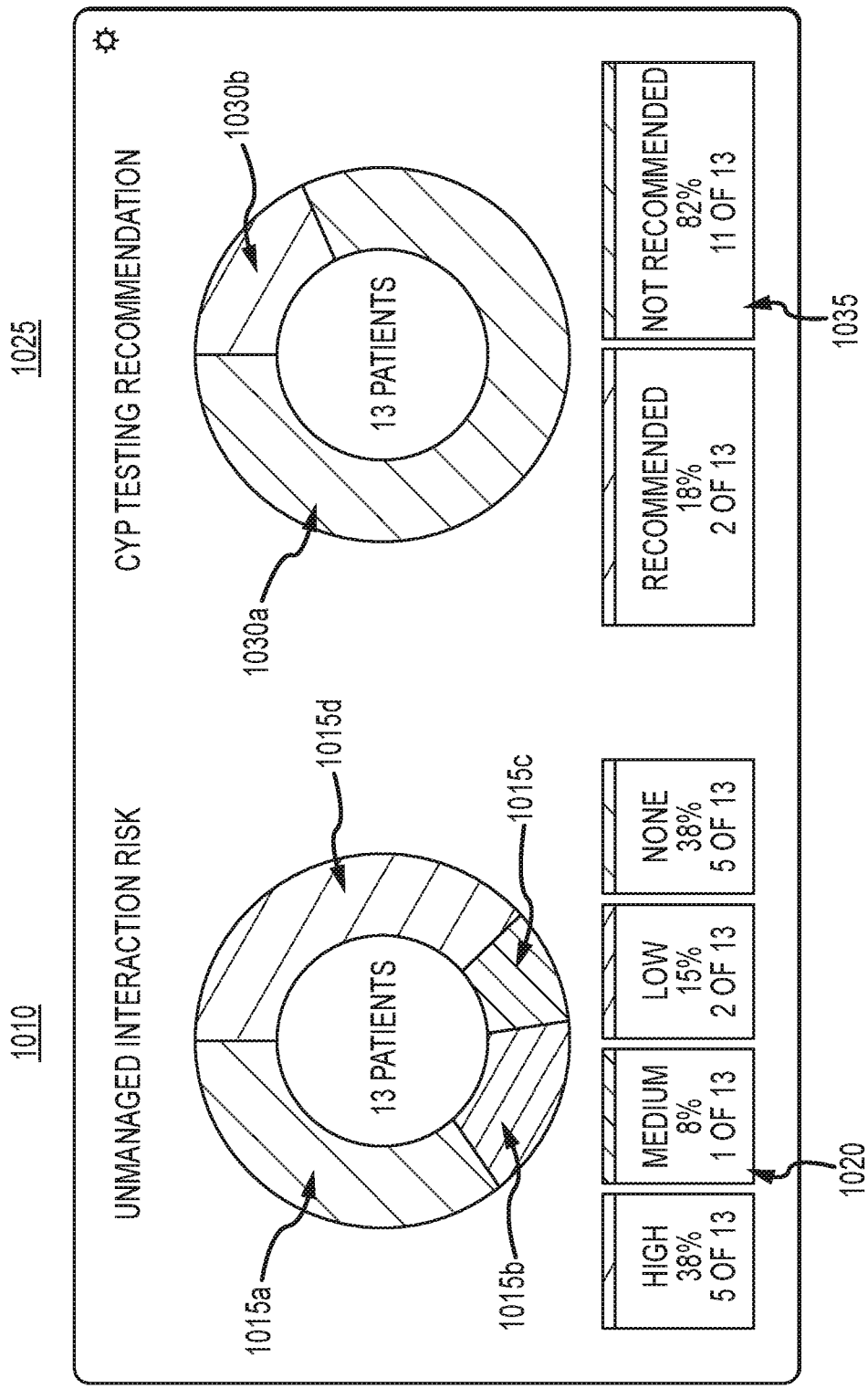
FIG. 12 is an example display of unmanaged risk of a population in accordance with an embodiment of the invention.

FIG. 12 demonstrates that the system may also display aggregate data involving multiple individuals. This approach may be modified to handle cohorts of patients, such as all patients enrolled in a medical practice or seen at a particular institution. A group of hundreds of patients may be assessed for risk based on the absence of genetic information in their electronic medical records (EMRs). In the example illustrated in FIG. 12, 13 patients are assessed based on CYP2D6, CYP2C9, and CYP2C19 profiles. The drug list for each patient may be considered in assessing possible risk with the system as described above. The risk may then be pooled. The unmanaged interaction risk chart 1010 may be a ring divided into multiple segments 1015a-d. Each segment 1015a-d may be color coded or textured differently based on the severity of the risk of an adverse drug event occurring, and each segment 1015a-d may be sized based on the number of patients in the pool that are included in that risk segment. In the example illustrated in FIG. 12, segment 1015a corresponds to no risk, segment 1015b corresponds to low risk, segment 1015c corresponds to medium risk, and segment 1015d corresponds to high risk. The risk in chart 1010 may be due to drug-drug or drug-gene interactions. An information bar 1020 may appear below the chart 1010, which provides the risk information contained in the chart 1010 in text form. The CYP testing recommendation chart 1025 may also be a ring divided into multiple segments 1030a-b. Each segment 1030a-b may be color coded or textured differently based on whether or not genetic testing is recommended, and sized based on the number of patients in the pool that are included in that segment. In the example illustrated, segment 1030a corresponds to genetic testing not recommended, and segment

1030b corresponds to genetic testing is recommended. An information bar 1035 may appear below chart 1025 which provides the information contained in the chart 1025 in text form. The two charts 1010, 1025 in combination may provide an easy to understand display of information regarding potential adverse drug events and which adverse drug events may be related to genetics. In the example illustrated in FIG. 12, although 38% of the patients may need adjustments to their treatment to reduce the risk of adverse drug events, only two would benefit from having genetic testing done to confirm drug-gene interactions. This allows medical care providers to focus their attention on the most at-risk patients and only invest in genetic testing where it may be most beneficial to patient outcomes.

The display provided by the system may be configured such that a user may be able to select a segment 1015, 1030 of either of the charts 1010, 1025. Selection may be made by using a cursor controlled by a mouse or with a finger on a touch-sensitive display, for example. Once a segment is selected, the user may be provided with more detailed information. For example, a list of individuals contained in that segment may appear. An example of an individual list 1100 is shown in FIG. 13. The individual list 1100 may include the patient name column, risk probability column, and/or an evidence column. The evidence column may be used as an additional or optional method of ranking patients. The evidence column indicates what type of evidence is available on the patient's risk. In the example illustrated in FIG. 13, four stars is indicative of a Food and Drug Administration (FDA) boxed warning; three stars is indicative of a notice in a product insert; two stars is indicative of a clinical study; and one star is indicative of a prediction generated by an algorithm used by the system. Other classification methods of evidence may also be used. In some embodiments, the evidence classification may be combined with other factors, such as those described previously, to generate a risk score for a patient. Selecting an individual from the individual list 1100 may allow the user to access the individual's interaction report 800.

The risk assessment display described above in FIG. 12 may be updated or toggled to show the risk-reduction effect of eliminating missing genetic data by performing genetic testing, or by other modifications to treatments, for example, change medications. A display of this type may be used by an actuary, for example, to assess the effect of changes in a medical practice or drug formularies such as to assess the impact of electronic medication management practice on risk of causing harm in a medical practice.

Embodiments of the invention may also be used as a prescription management service that incorporates smart tools for alerting the user to interactions, including both known and unknown interactions, and for managing or avoiding any associated medication risks. Predictive algorithms may be used to generate genetic risk profiles. Embodiments may also serve to alert the user to the potential cost of not collecting genetic information on an individual. Depending on the kind of medications typically prescribed, some practices may have more risk than others, and this enhanced risk burden may be calculated in the aggregate data.

Sources of risk information for validating predictive algorithms include data downloaded from medical records, and may include information concerning hospital incidents and adverse events, coding data recorded under international classification of diseases, 9th revision ("ICD-9"), and healthcare procedural coding system ("HCPCS") entries. Further, all dedicated databases may be implemented as relational, hierarchical or object-oriented databases, or may be implemented using custom file indexing structures and processes.

In one embodiment, the system "de-identifies" specific patient information from any of its aggregated reports or analyses, to protect particular patient information while maintaining demographic and systemic information for aggregated analysis, benchmarking, trending and/or prediction of data from databases. Aggregated data analysis facilitates better understanding of certain risks and costs associated with patient processing within a medical system, promoting better decision-making as to applying risk management and quality compliance resources; it may further facilitate demonstrating the impact of changes to patient processing, over time (i.e., trending), so as to reduce the costs and operations associated with negative outcomes. Such aggregate de-identified results may be used by institutions, insurance carriers, or national governments to improve healthcare outcomes.

Figure 14:
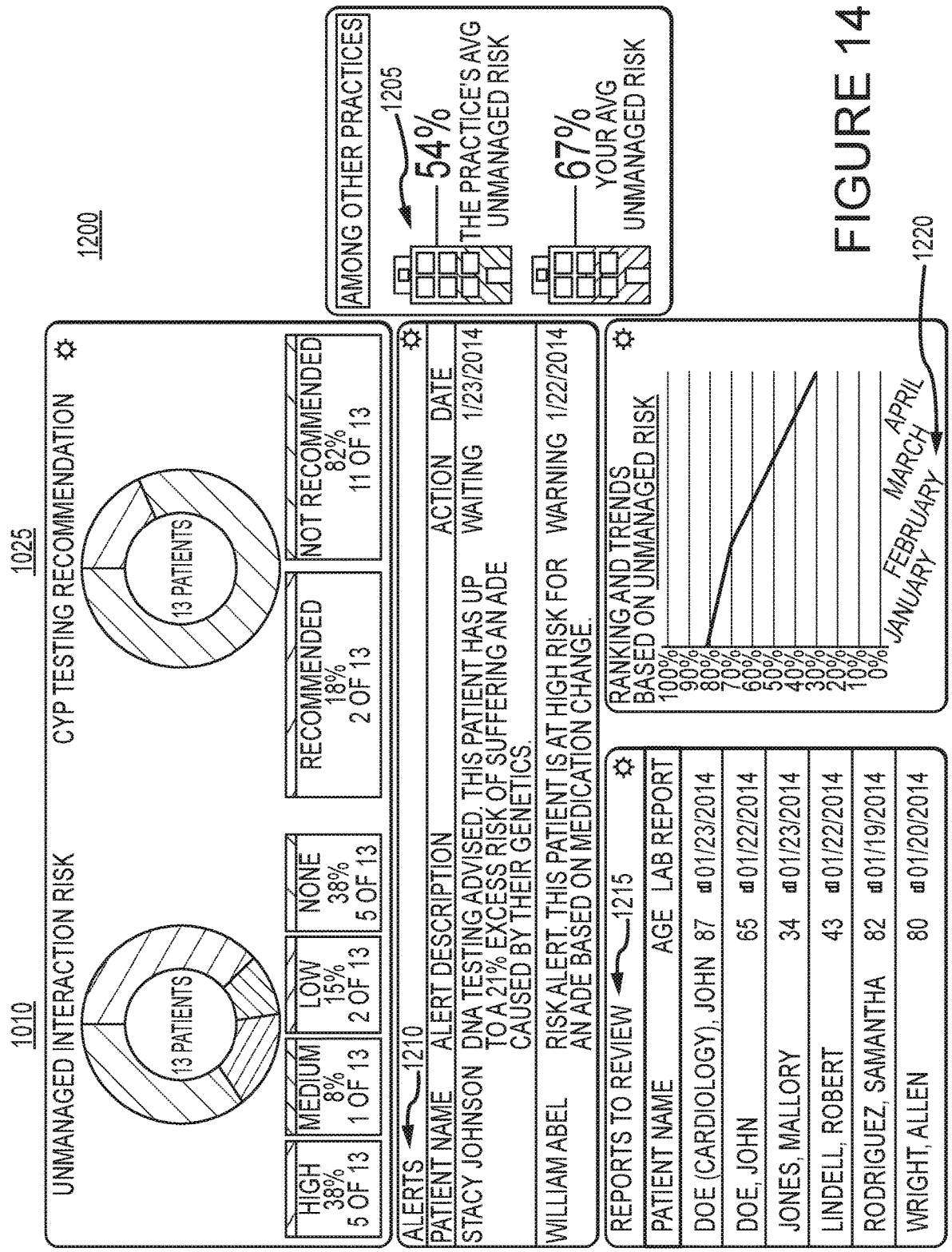
FIG. 14 is an example dashboard in accordance with an embodiment of the invention.

The display elements described above and illustrated in FIGS. 9-13 may be used as elements in a dashboard 1200 illustrated in FIG. 14. The dashboard 1200 may be customizable by a user or clinical practice. The dashboard may display one or more of the elements contained in FIGS. 9-13. It may also include additional elements such as alerts 1210, reports 1215, and other graphical representations of risk. For example, element 1205 is a graphical representation comparing the unmanaged risk levels between two different practices. Unmanaged risk is either known or unknown risk that has not been acted upon by an individual or medical care provider. Not all risks can be eliminated, but risk can be managed by reducing unknown risks when possible and making changes to treatment plans when indicated by the risk factors, Another example element that may be included is a trend line 1220. The trend line 1220 allows a user to view the change in unmanaged risk over time.

Figure 15:
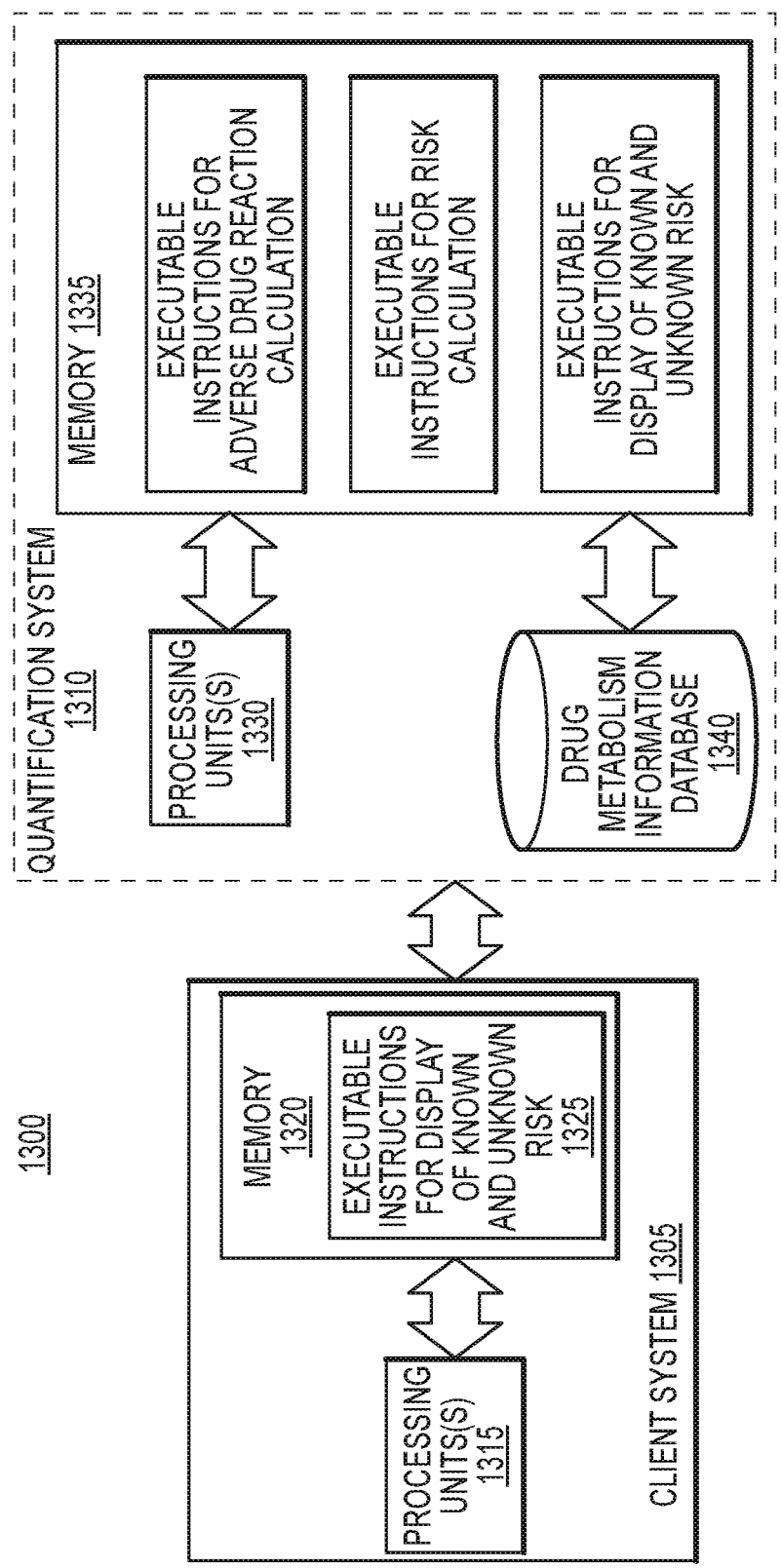
FIG. 15 is a schematic illustration of an example computing system arranged in accordance with embodiments of the present invention.

FIG. 15 is a schematic illustration of an example computing system arranged in accordance with embodiments of the present invention, such as those described above. The system 1300 includes a client system 1305 and a quantification system 1310. The client system 1305 includes processing unit(s) 1315 and memory 1320. The quantification system 1310 including processing unit(s) 1330 and memory 1335. Generally, any number or type of processing unit(s) may be used to implement the processing unit(s) 1315 and 1330. For example, any number of processors may be used, or in some examples dedicated circuitry to provide one or more functions described herein may be used. Any type of memory may generally be used to implement the memory 1320 and 1335. For example, RAM, ROM, flash, disk drives, solid state drives, or combinations thereof may be used. The memory 1335 may be encoded with executable instructions for quantifying known and unknown risk of an effect on drug metabolism (or other outcome). The memory 1335 may additionally or instead be encoded with executable instructions for display of known and unknown risk.

The client system 1305 and quantification system 1310 may be in electronic communication, e.g. over a network such as the internet or a local area network. It is to be understood that computing systems described herein may be quite flexible for examples of the present invention. For example, in some cases a separate client system may not be used, and a client may enter and/or view information directly from the quantification system 1310. In some examples, the quantification system 1310 may be implemented using a cloud service, such that a dynamic amount of processing power may be available and allocation of computational workload among processing unit(s) may be performed in accordance with methods described herein.

The client system 1305 may be implemented using any of a variety of computing devices including, but not limited to, a desktop computer, laptop computer, cellular telephone, electronic tablet, personal data assistant, watch, appliance, or combinations thereof. The quantification system 1310 may be implemented using any of a variety of computing devices including, but not limited to, a server, multiple servers, a cloud service, a desktop, a laptop, or combinations thereof.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

While the above is a complete description of selected embodiments of the present invention, it is possible to practice the invention use various alternatives, modifications, combinations and equivalents. In general, in the following claims, the terms used in the written description should not be construed to limit the claims to specific embodiments described herein for illustration, but should be construed to include all possible embodiments, both specific and generic, along with the full scope of equivalents to which such claims are entitled. Accordingly, the claims are not limited by the disclosure.

What is claimed is:

1. A method comprising:
    receiving, by a processor, identification of at least one drug;
    selecting, using the computing system, certain factors affecting exposure of an individual to the at least one drug, wherein the certain factors include a genotype and one or more of hospital incident data, adverse event data, medical coding data, or combinations thereof;
    quantifying, by the processor, an expected effect on metabolism of the at least one drug by the individual due to the certain factors by:
        identifying, by the processor, one or more possible values of at least one certain factor; and
        weighting, by the processor, the expected effect using each of the one or more possible values based on a matrix of probabilities of phenotypes;
    generating, by the processor, a numerical representation of risk based at least in part on the expected effect by weighting a severity of the expected effect;
    displaying, by the processor, the numerical representation of risk in an interaction report;
    pooling, by the processor, a respective numerical representation of risk associated with the at least one drug for each patient of a patient population, wherein the patient population includes the individual;
    determining, by the processor, that one or more patients in the patient population are recommended for genetic testing based on the respective numerical representation of the risk for each of the one or more patients; and
    displaying, by the processor, a genetic testing recommendation chart indicating a portion of the patient population, the portion of the patient population comprising the one or more patients in the patient population recommended for genetic testing.

2. The method of claim 1, wherein the certain factors further comprise a patient phenotype, liver function, kidney function, gender, weight, age, ethnicity, or combinations thereof.

3. The method of claim 1, wherein quantifying the expected effect on metabolism of the at least one drug comprises identifying a metabolic route used to metabolize the at least one drug.

4. The method of claim 1, further comprising generating by the processor, a second numerical representation of risk based at least in part on prospective genetic testing for the individual to determine the genotype.

5. The method of claim 1, further comprising displaying, by the processor, a graphical indicator that genetic testing is recommended.

6. The method of claim 1, further comprising:
    displaying, by the processor, aggregate risk data representative of the patient population in the genetic testing recommendation chart, wherein the aggregate risk data is segmented based on a severity of risk of an adverse drug event occurring; and
    displaying, by the processor, a change in unmanaged interaction risk over time, wherein the unmanaged interaction risk is associated with the numerical representation of risk and comprises a known risk that has not been acted upon by the individual or a medical care provider, an unknown risk that has not been acted upon by the individual or the medical care provider, or both the known risk and unknown risk.

7. The method of claim 1, wherein quantifying the expected effect on metabolism of the at least one drug comprises compiling a matrix of expected effects by evaluating a plurality of interactions between the at least one drug and the certain factors.

8. A non-transitory computer readable medium encoded with executable instructions thereon that, when executed by at least one computing device, cause the at least one computing device to perform operations comprising:
    receiving identification of at least one drug;
    selecting certain factors affecting exposure of an individual to the at least one drug;
    quantifying an expected effect on metabolism of the at least one drug by the individual due to the certain factors by:
        identifying one or more possible values of at least one certain factor; and
        weighting the expected effect using each of the one or more possible values based on a matrix of probabilities of phenotypes;
    generating a numerical representation of risk based at least in part on the expected effect by weighting a severity of the expected effect;
    displaying the numerical representation of risk in an interaction report;
    pooling a respective numerical representation of risk associated with the at least one drug for each patient of a patient population, wherein the patient population includes the individual;
    determining that one or more patients in the patient population are recommended for genetic testing based on the respective numerical representation of risk for each of the one or more patients; and
    displaying a genetic testing recommendation chart indicating a portion of the patient population, the portion of the patient population comprising the one or more patients in the patient population recommended for genetic testing.

9. The non-transitory computer readable medium of claim 8, wherein the operations further comprise displaying aggregate risk data representative of the patient population.

10. The non-transitory computer readable medium of claim 9, wherein the operations further comprise displaying the aggregated risk data in an unmanaged interaction risk chart segmented based on a severity of risk of an adverse drug event occurring, wherein unmanaged interaction risk is associated with the numerical representation of the risk and comprises a known risk, an unknown risk, or both that has not been acted upon by an individual or a medical care provider.

11. The non-transitory computer readable medium of claim 9, wherein the operations further comprise displaying the aggregated risk data in the genetic testing recommendation chart.

12. The non-transitory computer readable medium of claim 10, wherein the operations further comprise determining a change in the unmanaged interaction risk over time.

13. The non-transitory computer readable medium of claim 8, wherein the certain factors include a drug metabolizing enzyme, a glucuronosyltransferase enzyme, or a transporter protein.

14. A system comprising:
a memory comprising instructions stored thereon; and
a processor coupled to the memory, wherein the instructions, when executed by the processor, cause the processor to:
quantify an expected effect of a drug on an individual due to certain factors by:
identifying one or more possible values of at least one of the certain factors; and
weighting the expected effect using each of the one or more possible values based on a matrix of probabilities of phenotypes;
generate a numerical representation of risk based at least in part on the expected effect by weighting a severity of the expected effect;
determine an unmanaged interaction risk associated with the drug for a patient population, the patient population including the patient, based on the numerical representation of the risk;
pool the unmanaged interaction risk for the patient population;
determine that one or more patients in the patient population are recommended for genetic testing based on a value of the unmanaged interaction risk for each of the one or more patients being more than a predetermined threshold;
display an unmanaged interaction risk chart segmented based on a severity of risk of an adverse drug event occurring; and
display a genetic testing recommendation chart including one or more segments, wherein at least one segment indicates a portion of the patient population, the portion of the patient population comprising the one or more patients in the patient population recommended for genetic testing.

15. The system of claim 14, wherein the instructions further cause the processor to display a risk-reduction effect of missing genetic data in response to a user toggling the unmanaged interaction risk chart or the genetic testing recommendation chart, wherein the risk-reduction effect is based on performing genetic testing, modification to a treatment, or change in medication.

16. The system of claim 14, wherein the instructions further cause the processor to display one or more visual indicators on the unmanaged interaction risk chart indicating a severity of the adverse drug event.

17. The system of claim 14, wherein the instructions further cause the processor to display one or more visual indicators on the genetic testing recommendation chart indicating whether genetic testing is recommend.

18. The system of claim 14, wherein the instructions further cause the processor to display a text representation of the unmanaged interaction risk chart and/or the genetic testing recommendation chart.

19. The system of claim 14, wherein the numerical representation of the risk corresponds due to drug-drug interaction or drug-gene interaction.

20. The system of claim 14, wherein unmanaged interaction risk is associated with the numerical representation of risk and comprises a known risk that has not been acted upon by a patient of the plurality of patients or a medical care provider, an unknown risk that has not been acted upon by the patient of the plurality of patients or the medical care provider, or both the known risk and unknown risk.

* * * * *